United States Patent
Erneta et al.

(10) Patent No.: US 9,149,558 B2
(45) Date of Patent: *Oct. 6, 2015

(54) ANTIMICROBIAL POLYMER COMPOSITIONS AND THE USE THEREOF

(75) Inventors: Modesto Erneta, Princeton Junction, NJ (US); Robert DiLuccio, Haymarket, VA (US)

(73) Assignee: Ethicon, Inc., Somerville, NJ (US)

( * ) Notice: Subject to any disclaimer, the term of this patent is extended or adjusted under 35 U.S.C. 154(b) by 583 days.

This patent is subject to a terminal disclaimer.

(21) Appl. No.: 12/688,435

(22) Filed: Jan. 15, 2010

(65) Prior Publication Data

US 2010/0204411 A1   Aug. 12, 2010

Related U.S. Application Data

(63) Continuation-in-part of application No. 11/132,992, filed on May 19, 2005.

(51) Int. Cl.
| | |
|---|---|
| *A61L 17/00* | (2006.01) |
| *A01N 59/16* | (2006.01) |
| *A61L 17/10* | (2006.01) |
| *A61L 24/00* | (2006.01) |
| *A61L 24/04* | (2006.01) |
| *A61L 27/18* | (2006.01) |
| *A61L 27/54* | (2006.01) |
| *A61L 29/06* | (2006.01) |
| *A61L 29/16* | (2006.01) |
| *A61L 31/06* | (2006.01) |
| *A61L 31/16* | (2006.01) |
| *C08G 63/68* | (2006.01) |
| *C08G 63/91* | (2006.01) |
| *C08L 67/04* | (2006.01) |
| *C08K 5/00* | (2006.01) |

(52) U.S. Cl.
CPC ............... *A61L 17/005* (2013.01); *A01N 59/16* (2013.01); *A61L 17/105* (2013.01); *A61L 24/0015* (2013.01); *A61L 24/046* (2013.01); *A61L 27/18* (2013.01); *A61L 27/54* (2013.01); *A61L 29/06* (2013.01); *A61L 29/16* (2013.01); *A61L 31/06* (2013.01); *A61L 31/16* (2013.01); *C08G 63/681* (2013.01); *C08G 63/91* (2013.01); *C08L 67/04* (2013.01); *A61L 2300/102* (2013.01); *A61L 2300/104* (2013.01); *A61L 2300/404* (2013.01); *A61L 2300/606* (2013.01); *A61L 2300/80* (2013.01); *C08K 5/0058* (2013.01); *C08K 5/0091* (2013.01)

(58) Field of Classification Search
CPC ...... A61L 17/145; A61L 17/12; A01N 59/16; A01N 25/10; A01N 37/46
See application file for complete search history.

(56) References Cited

U.S. PATENT DOCUMENTS

| | | | |
|---|---|---|---|
| 3,284,417 A | 11/1966 | Hostettler | |
| 3,942,532 A | 3/1976 | Hunter et al. | |
| 4,095,600 A | 6/1978 | Casey et al. | |
| 4,122,129 A | 10/1978 | Casey et al. | |
| 4,181,786 A * | 1/1980 | Mune et al. | 525/161 |
| 4,201,216 A | 5/1980 | Mattei | |
| 4,289,873 A | 9/1981 | Kubo et al. | |
| 4,994,074 A | 2/1991 | Bezwada et al. | |
| 5,644,002 A | 7/1997 | Cooper et al. | |
| 5,668,288 A | 9/1997 | Storey et al. | |
| 6,153,210 A | 11/2000 | Roberts et al. | |
| 6,878,757 B2 | 4/2005 | Roby | |
| 6,881,766 B2 | 4/2005 | Hain | |
| 2004/0127676 A1 | 7/2004 | Cazaux | |
| 2004/0153125 A1 | 8/2004 | Roby | |
| 2004/0162580 A1 | 8/2004 | Hain | |
| 2004/0185250 A1 | 9/2004 | John | |
| 2005/0100574 A1 | 5/2005 | Furukawa et al. | |
| 2006/1026333 | 11/2006 | Erneta et al. | |
| 2007/0031503 A1 | 2/2007 | Hirakura et al. | |

FOREIGN PATENT DOCUMENTS

| | | |
|---|---|---|
| EP | 0437095 A | 8/1999 |
| WO | 96/01231 A1 | 1/1996 |
| WO | 2004/052314 A2 | 6/2004 |
| WO | 2004/054503 A2 | 7/2004 |
| WO | 2005/049101 A1 | 6/2005 |
| WO | 2006125125 A2 | 11/2006 |

OTHER PUBLICATIONS

Bendix, Dieter. "Chemical synthesis of polylactide and its copolymers for medical applications." Polymer Degradation and Stability 59.1 (1998): 129-135.*

Multanen M. et al.: "Bacterial; Adherence to Silver Nitrate Coated Poly-L-Lactic Acid Urological Stents in Vitro." Urological Research Oct. 2000, vol. 28, No. 5, Oct. 2000, pp. 327-331, XP002451300.

Multanen Markku et al.: "Biocompatibility Encrustation and Biodegredation of Ofloxacine and Silver Nitrate Coated Poly-l-Lactic Acid Stents in Rabbit Urethra" Urological Research, vol. 30, No. 4, Sep. 2002 pp. 227-232, XP002451301.

Multanen M. et al.: "Biocompatibility of Silver Nitrate and Ofloxacine Coated Bioabsorbable SR-PLLA Rods." Urological Research, vol. 29, No. 2, Apr. 2001, pp. 113-117, XP002451302.

Bhargava, H. et al., American Journal of Infection Control, 209-218 (1996).

Purification of Laboratory Chemical (Butterworth-Heinemann, Elsevier, 5th Edition, 2003, p. 84).

U.S. Appl. No. 11/132,992, filed May 19, 2005.

* cited by examiner

*Primary Examiner* — Bethany Barham
*Assistant Examiner* — Peter Anthopolos
(74) *Attorney, Agent, or Firm* — Roberts Mlotkowski Safran & Cole, PC

(57) ABSTRACT

An antimicrobial composition comprising an ionic complex of an anionic polyester with an antimicrobial metal, wherein the anionic polyester has an ion exchange capacity from about 0.19 meq/g to about 1.0 meq/g.

15 Claims, No Drawings

ANTIMICROBIAL POLYMER COMPOSITIONS AND THE USE THEREOF

This application is a continuation-in-part of and claims benefit under 35 U.S.C. §120 to copending application U.S. Ser. No. 11/132,992, filed May 19, 2005, which is incorporated by reference herein in its entirety.

FIELD OF THE INVENTION

The present invention relates generally to polymer compositions and their use for making or coating articles, such as medical devices. More specifically the invention relates to antimicrobial compositions that are complexes of an anionic polymer with an antimicrobial metal. Further, the present invention relates to complexes of anionic polyester with silver, which may be used alone or in combination with medical devices. The present invention also relates to medical devices utilizing such antimicrobial compositions.

BACKGROUND OF THE INVENTION

Whenever a medical device is used in a surgical setting, a risk of infection is created. The risk of infection dramatically increases for invasive or implantable medical devices, such as intravenous catheters, arterial grafts, intrathecal or intracerebral shunts and prosthetic devices, which create a portal of entry for pathogens while in intimate contact with body tissues and fluids. The occurrence of surgical site infections is often associated with bacteria that colonize on the medical device. For example, during a surgical procedure, bacteria from the surrounding atmosphere may enter the surgical site and attach to the medical device. Bacteria can use the implanted medical device as a pathway to surrounding tissue. Such bacterial colonization on the medical device may lead to infection and morbidity and mortality to the patient.

A number of methods for reducing the risk of infection associated with invasive or implantable medical devices have been developed that incorporate antimicrobial metals or metal salts into the medical devices. Such devices desirably provide effective levels of the antimicrobial metal while the device is being used.

For many years silver and silver salts have been used as antimicrobial agents in medical applications. Such medical applications include the use of aqueous silver nitrate solutions to prevent eye infection in newborn babies. Silver salts have also been used to prevent and control infection such as conjunctivitis, urethritis, and vaginitis.

Additionally, silver and silver salts have been used as antimicrobial agents in conjunction with medical devices, such as catheters, cannulae, and stents. Typically, the silver or silver salt is deposited directly onto the surface of the medical device via conventional coating techniques, such as vapor coating, sputter coating, or ion beam coating.

For example, WO 2004054503A2 and U.S. Pat. No. 6,878,757 to Roby describe antimicrobial coatings applicable to sutures where the coating comprises (i) mixtures of caprolactone copolymers and silver stearate, and (ii) mixtures of copolymers of epsilon-caprolactone, bioabsorbable monomer and sodium stearoyl lactylate or the silver salt of stearoyl lactylate, respectively. The silver salt in both of these references remains in a salt form in the copolymer matrix, and silver ions are released into a target environment from the coating by solubilization of the silver salt in the target environment. In turn, the solubility of the silver salt is a function of the nature of environment where it is delivered, and factors such as counter-ion concentration and ionic strength of the target environment.

U.S. Pat. No. 6,881,766 to Hain describes sutures fabricated from and/or coated with compositions including water-soluble glass. The water-soluble glass optionally includes a therapeutic agent, e.g., silver, to promote wound repair. The silver in this case may be incorporated in the form of an inorganic silver salt such as silver oxide, silver nitrate or silver orthophosphate. Similar to the reference described above, the release of the silver ions into the target environment may be dependent upon the solubility of the silver salt in the target environment.

Other metals, such as zinc, copper, magnesium and cerium, have also been found to possess antimicrobial properties, both alone and in combination with silver, some of which exhibited synergistic benefits of their combinations. These and other metals have been shown to provide antimicrobial behavior even in minute quantities.

Other methods of coating antimicrobial metals or metal salts onto a substrate involve deposition or electro-deposition of the metal or metal salt from solution. Additional techniques for incorporating metal into a medical device include dipping, spraying or brushing a liquid solution of the metal or metal salt onto a polymer, for example, in pellet form, prior to processing the medical device. Alternatively, a solid form of the metal or metal salt can be mixed with a finely divided or liquefied polymeric resin, which is then molded into the article. Also, the metal or metal salt can be mixed with monomers of the material prior to polymerization.

However, problems associated with medical devices having metal or metal salts deposited thereon by conventional incorporation techniques include poor adhesion of the metal or metal salt on the medical device, and lack of uniformity in the concentration of the metal or metal salt throughout the coating. Also, it is believed that deposition or electro-deposition of the antimicrobial metal onto a medical device produces coatings that do not release the metal from the coating easily, and therefore require direct contact with microbes in the tissue to have an antimicrobial effect.

U.S. Pat. No. 6,153,210 to Roberts et al. discloses polymeric microparticles containing metal ions, preferably silver ions, for control of periodontal disease. The microparticles can be made from poly(lactide-co-glycolide) (PLGA) having MW of about 12,000 Daltons, with which the metal ions are mixed or complexed. However, Roberts et al. are silent as to the ion exchange capacity of their polymers, and as to PLGA having MW of less than about 10,000 Daltons.

Therefore, there is a need to provide an antimicrobial composition where the release mechanism of metal ions into the target environment is not dependent upon solubilization in the target environment. More particularly, there is a need for an antimicrobial composition that exhibits immediate activity upon contact with fluids in the human body. Additionally, it is desirable to have an antimicrobial composition that adheres well to medical devices, as well as antimicrobial medical devices having a uniform distribution of metal or metal salts throughout.

SUMMARY OF THE INVENTION

In one embodiment, the present application is directed to an antimicrobial composition comprising an ionic complex of an anionic polyester with an antimicrobial metal, wherein the anionic polyester has an ion exchange capacity from about 0.19 meq/g to about 1.0 meq/g.

In another embodiment, the antimicrobial composition has an anionic polyester having a weight average molecular weight (Mw) between about 2000 and about 7200 Daltons.

In another embodiment, the composition contains from about 20,000 ppm to about 96,000 ppm by weight of the antimicrobial metal.

Conveniently, the anionic polyester is prepared from a ring-opening polymerization of aliphatic lactone monomers polymerized in the presence of an organometallic catalyst and an anionic initiator.

Preferably, the aliphatic lactone monomer is selected from the group consisting of glycolide, trimethylene carbonate, L-lactide, D-lactide, DL-lactide, mesolactide, ε-caprolactone, p-dioxanone, 1,3-dioxan-2-one, δ-valerolactone, β-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one and combinations thereof.

Advantageously, the anionic initiator is selected from the group consisting of alpha-hydroxy acids, glycolic acid, D-lactic acid, DL-lactic acid, L-lactic acid, β-hydroxyacids, γ-hydroxyacids, δ-hydroxyacids, ε-hydroxyacids, ε-hydroxycaproic acid, polyhydroxyacids, tartaric acid, citric acid and glucoronic acid, and is present at a mole ratio of lactone monomer to initiator between about 10 and 30.

Preferably, the mole ratio of lactone monomer to initiator is between about 10 and 25, and the antimicrobial metal is selected from the group consisting of Ag, Au, Pt, Pd, Ir, Sn, Cu, Sb, Bi, Zn, Ni, Mg, and Mn. More preferably, the antimicrobial metal is silver.

In another embodiment, the present application is directed to a medical device having an antimicrobial composition comprising: an ionic complex of an anionic polyester with an antimicrobial metal wherein the anionic polyester has an ion exchange capacity from about 0.19 meq/g to about 1.0 meq/g.

Advantageously, the medical device is in the form of a fiber, mesh, powder, microspheres, flakes, sponge, foam, fabric, nonwoven, woven mat, a film, suture anchor device, suture, catheter, staple, surgical tack, clips, plate and screw, drug delivery device, adhesion prevention barrier, and tissue adhesive.

Preferably, the anionic polyester has a weight average molecular weight (Mw) between about 2000 and about 7200 Daltons.

Conveniently, the composition contains from about 20,000 ppm to about 96,000 ppm by weight of the antimicrobial metal.

In another embodiment, the present application is directed to a method of making an ionic complex of an anionic polyester with an antimicrobial metal comprising: conducting a ring-opening polymerization of one or more aliphatic lactone monomers in the presence of an organometallic catalyst and an anionic initiator at a mole ratio of lactone monomer to initiator between about 10 and 30; recovering the anionic polyester which has an ion exchange capacity from about 0.19 meq/g to about 1.0 meq/g; conducting an ion exchange between carboxylic acid groups on said anionic polyester and said antimicrobial metal; and recovering said ionic complex of said anionic polyester and said antimicrobial metal.

Preferably, the aliphatic lactone monomer is selected from the group consisting of glycolide, trimethylene carbonate, L-lactide, D-lactide, DL-lactide, mesolactide, ε-caprolactone, p-dioxanone, 1,3-dioxan-2-one, δ-valerolactone, β-3-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one and combinations thereof.

Advantageously, the anionic initiator is selected from the group consisting of alpha-hydroxy acids, glycolic acid, D-lactic acid, DL-lactic acid, L-lactic acid, β-hydroxyacids, γ-hydroxyacids, δ-hydroxyacids, ε-hydroxyacids, ε-hydroxycaproic acid, polyhydroxyacids, tartaric acid, citric acid and glucoronic acid.

Preferably, the antimicrobial metal is selected from the group consisting of Ag, Au, Pt, Pd, Ir, Sn, Cu, Sb, Bi, Zn, Ni, Mg, and Mn, and is more preferably silver.

In another embodiment, the ion exchange is conducted in a solution of said antimicrobial metal in an aqueous soluble alcohol selected from the group consisting of ethanol, n-propyl alcohol, and isopropyl alcohol.

DETAILED DESCRIPTION

The present invention provides an antimicrobial composition comprising an ionic complex of an anionic polymer with an antimicrobial metal. In one embodiment, the antimicrobial composition comprises a complex of an anionic polyester with an antimicrobial metal, wherein the anionic polyester molecules have at least one carboxylic acid group that may be linear or branched.

The term "complex" as used herein refers to an intimate mixture at the molecular scale, with ionic or electrostatic bonding between the antimicrobial metal ions and carboxylic acid groups of the anionic polymer. The complex preferably comprises a salt formed between the anionic polymer and metal ions.

The anionic polyester may be absorbable or nonabsorbable, and can be synthesized via ring opening polymerization of aliphatic lactone monomers. Specifically, the aliphatic lactone monomers are polymerized in the presence of an organometallic catalyst and an initiator. The ring-opening polymerization process is well-known in the art, as described in more detail in U.S. Pat. No. 4,289,873 to Kubo et al., the content of which is incorporated by reference as if set forth in its entirety.

Typical aliphatic lactone monomers that may be utilized to synthesize the anionic polyester described herein, and from which the repeating units of the anionic polyester are derived, are selected from the group consisting of glycolide, trimethylene carbonate, L-lactide, D-lactide, DL-lactide, mesolactide, ε-caprolactone, p-dioxanone, 1,3-dioxan-2-one, δ-valerolactone, β-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one and combinations thereof.

The organometallic catalysts include titanates and zirconates, and preferably organotin compounds such as stannous chloride and stannous octoate.

The initiators are compounds containing at least one carboxylic acid group, and at least one other reactive group such as an hydroxyl group or an amine. Typical initiators, suitable for the synthesis of an anionic polyester having carboxylic acid groups, are alpha-hydroxy acids such as glycolic acid, D-lactic acid, DL-lactic acid, L-lactic acid, β-hydroxyacids, γ-hydroxyacids, δ-hydroxyacids, and ε-hydroxyacids such as ε-hydroxycaproic acid. Preferable initiators contain at least one carboxylic acid group and a primary hydroxyl group, such as glycolic acid. The alcohol group readily participates in a reaction that incorporates the initiator in the growing chain. Typical initiators suitable for the synthesis of branched polyesters with at least one carboxylic acid group are the polyhydroxyacids, such as glucoronic acid.

In certain embodiments, the anionic polyester may have only one carboxylic acid group per molecule. Such anionic polyesters are described in U.S. Pat. Nos. 4,201,216 and 4,994,074, the entire content which is incorporated herein by reference The anionic polyesters include homopolymers and copolymers of lactide and glycolide, i.e., polylactide, polyglycolide, and copolymers of lactide and glycolide with each other and with other reactive monomers; poly(p-dioxanone); poly (alkylene oxalate); copolymers of vinyl acetates with unsaturated carboxylic acids such as crotonic, acrylic and methacrylic acids; and mixtures of such polymers. Particularly preferred polymers are the copolymers of lactide and glycolide, which contain from about 15 to 85% lactide, and have an inherent viscosity of from about 0.5 to 4.0 measured as a 0.1 percent solution in hexafluoroisopropanol at 25° C. These polymers are water-insoluble, rapidly absorbable, and soluble in many common organic solvents such as acetone, chloroform, toluene, xylene, and 1,1,2-trichloroethane.

It is also possible to produce other anionic polyesters in a similar fashion with terpolymers, tetramers, and the like, from building blocks including, but not limited to, glycolide, lactide, epsilon-caprolactone, trimethylene carbonate, and p-dioxanone.

According to the present invention, anionic polyesters which are particularly suitable for use in forming antimicrobial compositions can be formed in the ring-opening polymerization process by controlling the initiator ratio (IR). The term "initiator ratio" as used herein, refers to the total moles of monomer divided by the total moles of initiator. Generally, the lower the IR (i.e. the greater the amount of initiator relative to monomer), the lower the molecular weight of the polymer so-formed.

According to the present invention, the IR is preferably between about 10 to 30, or even between about 10 to 25, or even between about 10 to 15, which results in anionic polyesters having weight average molecular weights (Mw) of less than about 10,000 Daltons, preferably less than about 5,000 Daltons.

An anionic polyester which is a copolymer of epsilon-caprolactone and glycolide can be formed by using glycolic acid as an initiator and stannous octoate as the catalyst. The polymerization may be conducted in a batch process that allows the formation of a random copolymer. However, it is also possible to conduct the polymerization in such a way as to allow for the formation of a semi-block copolymer. The initiator ratio may be varied to allow one to obtain a molecular weight that makes the final copolymer in a useable form. For example, the initiator ratio may range from about 5 to about 600, corresponding to a number average molecular weight (Mn) of about 575 to about 43,000, respectively. When the anionic polyester is used to prepare a coating on a substrate such as a medical device, the initiator ratio may range from about 10 to 30, corresponding to a Mn of about 1,150 to about 3,450, respectively. The molecular weight of the copolymer can vary greatly depending on its ultimate application.

An anionic polyester which is a poly-(epsilon-caprolactone) that is polymerized with glycolic acid as an initiator, and is consequently terminated with a carboxylic acid group can be formed. For example, the initiator ratio may range from about 5 to about 600, corresponding to a Mn of about 575 to about 34,000, respectively. When the anionic polyester is used to prepare a coating on a substrate such as a medical device, the initiator ratio ranges from about 10 to about 30, corresponding to a Mn of about 1,150 to about 3,450, respectively.

An anionic polyester which is a copolymer formed from lactide and glycolide with glycolic acid as an initiator can be formed. The initiator ratio ranges from about 10 to about 200, which corresponds to a Mn of about 1,170 to about 22,000, respectively.

Where the number of carboxylic acid groups is desirably 2 or more, one can provide an initiator that will cause the anionic polyester to form, for example, a branched structure. Examples of such initiators include, but are not limited to, tartaric acid, citric acid and the like. The branched structure may have one or more carboxylic acid groups in one or more branches on the polymer backbone or side chain. They may even be in the form of a dendrimer or star structure.

Advantageously, the anionic polyesters of the present invention have unusually high ion exchange capacities (IEC), such as from about 0.19 meq/g to about 1.0 meq/g, preferably from about 0.24 to about 0.8 meq/g, or even from about 0.3 to about 0.8 meq/g; the higher the IEC, the greater the amount of antimicrobial metal which can be exchanged for the hydrogen atom of the free carboxylic acid groups of the polymer chains.

For example, the presently disclosed anionic polyesters can form antimicrobial compositions having from about 20,000 ppm to about 96,000 ppm, preferably from about 25,000 ppm to about 85,000 ppm, or even from about 30,000 ppm to about 85,000 ppm by weight (based on the composition as a whole) of antimicrobial metal.

The high IEC of the presently disclosed polymers is due in part to the relatively low molecular weights of the polymer chains, each of which is terminated by at least one free carboxylic acid group. Thus, on a per-unit weight basis, the anionic polyesters of the present invention have many more free carboxylic acid sites for ion exchange than do similar polymers of higher molecular weight.

The anionic polyesters formed by the presently disclosed process have weight average molecular weights (Mw) below about 10,000 Daltons, preferably below about 5,000 Daltons, or between about 1,000 to about 8,000 Daltons, or even between about 2,000 to about 7,200 Daltons. Assuming a normal molecular weight distribution, the Mw is about twice the number average molecular weight (Mn) of these anionic polyesters.

The IEC of the presently disclosed anionic polyesters is further enhanced by the selection of the above-disclosed anionic initiators, which have carboxylic acid groups on one end thereof, and at least one other reactive group, such as amine or hydroxyl, such that the other reactive group is incorporated into the anionic polyester backbone and the carboxylic acid group of the initiator is available for ion exchange.

For comparison, the PLGA polyester disclosed in Example 1 of U.S. Pat. No. 6,153,210 was examined. The PLGA is disclosed as being a 50:50 lactic:glycolic copolyester of MW 12,000, provided by Boehringer Ingelheim Chemicals as "RG502H". The specifications of RG502H are available from Boehringer Ingelheim Chemicals and indicate that the polyester has an acid number of 6 mg KOH/g. Back-calculations from this acid number reveal the following data for RG502H:

IR=72
Mn=9354
Mw~18,700
IEC=0.107 meq/g
Max ppm Ag=11,403.

Clearly the presently disclosed anionic polyesters have greatly increased IEC which permits much greater antimicrobial metal loadings and enhanced antimicrobial activity as compared to RG502H.

The antimicrobial metal ions (M) referred to herein are metal ions having antimicrobial efficacy, including but not limited to Ag, Au, Pt, Pd, Ir, Sn, Cu, Sb, Bi, Zn, Ni, Mg, and Mn. The source of the antimicrobial metal ion in the complex with the anionic polymer includes, but is not limited to, elemental metals, metal compounds, alloys or mixtures thereof.

Silver is especially potent as an antimicrobial metal against a broad spectrum of microorganisms. Preferably, the source of the antimicrobial metal in the complex with the anionic polymer is elemental silver, silver alloys, a silver compound or mixtures thereof. The silver compound referred to herein is a compound comprising a silver ion, linked to another molecule via a covalent or non-covalent linkage. Examples of silver compounds include, but are not limited to, silver salts formed by silver ion with organic acids (e.g. acetic acids and fatty acids) or inorganic acids, such as silver sulfadiazine ("AgSD"), silver oxide ("$Ag_2O$"), silver carbonate ("$Ag_2CO_3$"), silver deoxycholate, silver salicylate, silver iodide, silver nitrate ("$AgNO_3$"), silver paraminobenzoate, silver paraminosalicylate, silver acetylsalicylate, silver ethylenediaminetetraacetic acid ("Ag EDTA"), silver picrate, silver protein, silver citrate, silver lactate, silver acetate and silver laurate.

The complex of an anionic polyester and an antimicrobial metal may be made by treating an anionic polyester with a solution of the source of the antimicrobial metal. For example, the anionic polyester may be in the form of solid fibers, sheet, sponge or fabric. In certain embodiments, the anionic polyester is an ion exchanger. In other embodiments, the anionic polyester may be in free acid form, in which case for example, the source of the antimicrobial metal may be a salt of a weak acid, whereby the anionic polyester is at least partially complexed by the metal salt. When using silver salts of weak acids, for example, the silver ion is exchanged for a proton on the anionic polyester and part of the salt is converted to a weak acid. When silver salts are used in excess of the stoichiometric amount required by the anion exchanger, the mixture of weak acid and salt in the solution results in a buffered solution which maintains a fairly constant pH and controls the degree of exchange reaction. An equilibrium reaction is established whereby the silver ions are bound to the acid portion of the polyester and also to the salt molecules. The excess silver salts and the weak acid remain in solution, while silver ions remain bound to the solid anionic polyester. The solid anonic polyester is then conveniently separated from the liquid/silver solution. Similar processes are described in EP-A-0437095, the entire content of which is expressly incorporated herein by reference.

The exchange reaction can be carried out in water or alcohol alone but is preferably carried out in mixtures of water and alcohols. The use of a mixture of water and alcohol provides good solubility for weak acid salts, and the alcohol enhances the ability of the anionic polyester to swell during the exchange reaction. Thus the physical properties (e.g. the inherent mechanical strength) of the anionic polyester are retained. Isopropyl alcohol is the preferred alcohol because many of the above-mentioned silver salts have good solubility therein in combination with water. Preferably, the alcohol to water molar ratio is in the range of about 9:1 to 1:9. If the solution becomes too rich in alcohol, some salts may no longer be soluble particularly if the alcohol is other than methanol. Linear and branched $C_2$-$C_{12}$ mono- or polyalcohols, including, but not limited to, n-propyl alcohol and ethanol, are suitable alcohols.

The amount of metal salt used is generally about equal to or up to twice the stoichiometric amount of carboxylic acid content of the polyester. Alternatively, a second charge of a stoichiometric amount of metal salt can be used if the reaction is recharged with fresh solvent and salt after the first charge reaches a constant pH. The material with elevated pH is then washed to remove the excess metal salt and ions therefrom.

The antimicrobial composition of the present invention provide the advantage of varying release kinetics for the antimicrobial metal ions. These varying release kinetics allow for an initial release of antimicrobial metal that provides antimicrobial activity immediately upon insertion in an aqueous environment, followed by a continual, extended release of the antimicrobial metal from the composition, resulting in sustained antimicrobial activity over time for at least 12 days.

In a further aspect, the antimicrobial composition may optionally contain other components that improve the antimicrobial effectiveness of the composition, or that otherwise serve as active agents for other benefits. These components include, but are not limited to, additional antimicrobials, additional salts, any other excipients or active ingredients that provide the compositions with beneficial properties or enhance the antimicrobial activity of the compositions. Such components include, but are not limited to, antimicrobial agents, antibiotics, and other active ingredients.

The antimicrobial compositions described herein may be used to coat substrate materials. Additionally, they can be a part of the coating that contains the antimicrobial composition described herein. These coatings may comprise either a single layer or multiple layers. In another embodiment, the antimicrobial composition may also be applied to a preformed article or part of an article of manufacture as a coating. The coated article may be produced, for example, by dipping the article into the composition, coextruding the article, wire coating the article, or spraying the article with the composition and then drying the coated article.

The antimicrobial composition may be made separately, and then applied as a coating to a substrate such as a medical device. Alternately, the antimicrobial composition may be made in situ, for example, by first coating a substrate such as a medical device with the anionic polyester followed by in situ treatment with a solubilized salt of the antimicrobial metal, thus imparting antimicrobial properties to the substrate. Additionally, organic liquids such as organic solvents may be utilized to facilitate complexation of the antimicrobial metal and the anionic polyester.

The antimicrobial compositions described herein can be used alone or in combination with other polymer coatings to provide advantageous properties to the surface of the substrate. These compositions can also be used to deliver additional pharmaceutical agents that, for example, are antiinfective, anticoagulants, improve healing, are antiviral, antifungal, antithrombogenic or impart other properties to coated substrates.

The antimicrobial compositions can also be used to inhibit algae, fungal, mollusk, or microbial growth on surfaces. The antimicrobial compositions described herein may also be used as herbicides, insecticides, antifogging agents, diagnostic agents, screening agents, and antifoulants.

In another aspect, the present invention includes an article of manufacture that is a medical device that comprises the antimicrobial compositions described herein. In one embodiment, the antimicrobial composition can be used to form an article or a portion of the article, for example by spinning, molding, casting, or extrusion.

The antimicrobial composition can be utilized to manufacture a medical device including, but not limited to a fiber, mesh, powder, microspheres, flakes, sponge, foam, fabric, nonwoven, woven mat, a film, suture anchor device, suture, staple, surgical tack, clips, plate and screw, drug delivery device, adhesion prevention barrier, and tissue adhesive.

The medical device may be composed of one or more of the antimicrobial compositions of the present invention, alone or in combination with other polymeric components.

As discussed above, the antimicrobial metal may be complexed with the anionic polyester in an aqueous alcohol environment. In one embodiment, the antimicrobial metal may be incorporated into the anionic polyester prior to forming a substrate such as a medical device. In an alternative embodiment, the antimicrobial metal can be incorporated into the anionic polyester after the formation of a substrate such as a medical device. For instance, the anionic polyester may be complexed with the antimicrobial metal by dipping, soaking, spraying or coating a medical device with the antimicrobial metal dispersed in an aqueous alcohol environment, as shown in Examples 1 to 3.

Example 1

An anionic polyester was prepared by the polymerization of epsilon-caprolactone and glycolide, using glycolic acid as an initiator and a catalyst in the amounts given below:

| | |
|---|---|
| epsilon-caprolactone | 1.8208 moles |
| glycolide | 0.1789 moles |
| glycolic acid | 0.0666 moles (Initiator ratio 30) |
| catalyst: | Stannous octoate 0.33 molar in toluene |

The anionic polyester was dissolved in ethyl acetate to make a 7% solids solution. Thereafter, a size 2/0 polyglactin 910 suture was immersion coated and air dried. The suture had 2.716 weight % coating.

In a bottle covered with aluminum foil, 201 grams of deionized water and 8 grams of isopropanol were mixed. Thereafter, 1.462 grams of silver acetate was added to the aqueous alcohol solution and mixed with a magnetic stirrer for 1½ hours. 20 more grams of isopropyl alcohol was added and mixed to produce a silver salt solution. The size 2/0 coated polyglactin 910 suture was immersed in a 50 gram aliquot of the silver salt solution at room temperature for 5 hours. The suture was rinsed by immersion in deionized water and vacuum dried at room temperature to produce a suture having the antimicrobial composition as a coating thereon. The amount of silver in the complex of the anionic polyester and silver was calculated as 30,480 ppm by weight.

Silver has a minimum inhibitory concentration (MIC) against $E.\ Coli$ of 10 ppm, as measured in a suitable growth medium and as described by Bhargava, H. et al in the American Journal of Infection Control, June 1996, pages 209-218. The MIC for a particular antimicrobial agent and a particular microbe is defined as the minimum concentration of that antimicrobial agent that must be present in an otherwise suitable growth medium for that microbe, in order to render the growth medium unsuitable for that microbe, i.e., the minimum concentration to inhibit growth of that microbe.

A demonstration of this MIC is seen in the disk diffusion method of susceptibility. A filter paper disk, or other object, impregnated with a pre-selected amount of a particular antimicrobial metal is applied to an agar medium that is inoculated with the test organism. The antimicrobial metal diffuses through the medium, and as long as the concentration of the antimicrobial metal is above the minimum inhibitory concentration (MIC), none of the susceptible microbe will grow on or around the disk for some distance. This distance is called a zone of inhibition. Assuming the antimicrobial metal has a diffusion rate in the medium, the presence of a zone of inhibition around a disk impregnated with an antimicrobial agent indicates that the organism is inhibited by the presence of the antimicrobial metal in the otherwise satisfactory growth medium, the diameter of the zone of inhibition is inversely proportional to the MIC.

The antimicrobial efficacy was evaluated by zone of inhibition assay, in which the sutures were cut into a 5 cm section. A Petri dish containing nutrient agar inoculated with about $10^5$ cfu/ml. A portion of 20 ml of TSA tempered at 47° C. was added into the Petri dish. The inoculum was mixed thoroughly with the growth medium and the suture was placed in the middle of the dish. The inoculated dish was incubated at 37° C. for 48 hr and the zone of inhibition was measured with a digital caliper.

The zone of inhibition assay was performed against $E.\ coli$ over a two-day period. The results indicate that the suture having the complex as a coating thereon exhibited a zone of inhibition against $E.\ Coli$ of 4.5 mm that was sustained for 12 days.

Example 2

A polycaprolactone polymer containing a carboxylic acid group was prepared utilizing glycolic acid, at an initiator ratio of 30, and a catalyst in the amounts given below:

| | |
|---|---|
| epsilon-caprolactone | 5000 grams |
| glycolic acid | 111.048 grams |
| catalyst: | Stannous octoate 0.33 molar solution in toluene |

The anionic polyester had a molecular weight Mw=6600 and an inherent viscosity in HFIP of 0.4 dl/g.

The anionic polyester was dissolved in ethyl acetate to make a 7% solids solution. Thereafter, a size 0 braided polyester suture was dipped into the anionic polyester/ethyl acetate solution, and the ethyl acetate was evaporated thereafter. The coating content of the suture was 2.65% by weight.

The anionic polyester coated suture was immersed in isopropanol for 10 minutes. Thereafter, it was immersed for 6 hours in a silver acetate water solution containing 0.943% silver acetate and 4.716% isopropanol. The suture was then washed with deionized water and vacuum dried to produce a suture having the antimicrobial composition as a coating thereon. The amount of silver in the complex of the anionic polyester and silver was calculated as 35,200 ppm by weight.

The antimicrobial efficacy was evaluated by a zone of inhibition assay as described in Example 1. The zone of inhibition assay was performed against $E.\ coli$ over a two-day period. The results indicate that the suture having the complex as a coating thereon exhibited a zone of inhibition against $E.\ Coli$ of 6.8 mm after 24 hours.

Example 3

A 65/35 lactide/glycolide anionic polyester was prepared using glycolic acid initiator at a monomer to initiator mole ratio of 30. The catalyst was a 0.33 molar solution of stannous octoate in toluene. A monomer/catalyst mole ratio of 25,000 was used.

The reactant amounts were:

| L(−) lactide | 1.3 moles |
|---|---|
| Glycolide | 0.7 moles |
| Glycolic acid | 0.0666 moles |
| Catalyst: | Stannous octoate solution 0.33 molar solution of toluene |

A coating dispersion of the anionic polyester and calcium stearate in ethyl acetate (4.5 weight % copolymer and 4.5 weight % calcium stearate) was prepared with high shear mixing. A size 2/0 uncoated polyglactin 910 suture was dip coated in the suspension and the ethyl acetate was evaporated. The coating content of the suture was 4.07% by weight.

The anionic polyester coated suture was immersed for 5 hours in a silver acetate water solution containing 0.634% silver acetate and 12.18% isopropyl alcohol. It was washed with deionized water and vacuum dried to produce a suture having the antimicrobial composition as a coating thereon. The amount of silver in the complex of the anionic polyester and silver was calculated as 27,700 ppm by weight.

The antimicrobial efficacy was evaluated by a zone of inhibition assay as described in Example 1. The zone of inhibition assay was performed against E. coli over a two-day period. The results indicate that the suture having the complex as a coating thereon exhibited a zone of inhibition against E. Coli of 1.7 mm after 24 hours.

Example 4

In this example, the direct conversion of the anionic polyester to a complex of an anionic polymer with an antimicrobial metal is accomplished prior to placement on a substrate such as a medical device.

Two samples were prepared, an Inventive Sample that uses the anionic polyester technology of this invention and a second example that uses a non-ionic polyester of the same copolymer.

Inventive Sample

An anionic polyester composed of 90/10 caprolactone/glycolide was synthesized by using a glycolic acid initiator at a molar ratio of monomer to initiator of 43. A film was prepared as follows:

Two grams of the anionic polyester were ground and wetted with 0.3 grams of isopropanol. The solids were then admixed with a silver acetate water solution, containing 0.0619 grams silver acetate in 10 grams of water. After two hours, the complex of the anionic polymer with silver was recovered by filtration and dried under vacuum at room temperature. About 1.5 grams of the complex was placed on a Teflon lined 0.010" mold. The mold was kept in an oven at 40° C. for about 10 minutes to facilitate film formation.

Comparative Sample

A nonionic polyester composed of 90/10 caprolatone/glycolide was synthesized by using mannitol as an initiator, as described in U.S. Patent Application 2004/0153125. Silver was added as a salt dispersed into molten nonionic polyester coating and converted into a film. About 1.5 grams of the mixture was placed on a Teflon lined 0.010" mold. The mold was kept in an oven at 40° C. for about 10 minutes to facilitate film formation.

The antimicrobial efficacy was evaluated by a zone of inhibition assay, as described in Example 1 except that the films were cut into 1 sq. cm section. The zone of inhibition assay was performed against S. aureus, E. coli and P. aeruginosa over a two-day period. The results are shown below.

Zone of Inhibition Test

| Sample | S. aureus | E. coli | P. aeruginosa |
|---|---|---|---|
| (a) 2% Ag ion exch in Cap/Gly | − | ++ | + |
| (b) 2% Ag based on Ag acetate in Cap/Gly | − | + | − |

++ medium inhibition (small but clear zone around test article)
+ low inhibition (unclear clear zone around test article)
− No inhibition (no inhibition zone)
(a) Cap/Gly initiated with Glycolic acid (Inventive Sample)
(b) Cap/Gly initiated with Mannitol (Comparative Sample)

Log Reduction

In this test, one side of the film was exposed to about 2000 CFU/0.5 sq. cm S. aureus in 10 ul saline with 20% serum for 60 min. The log reduction is the difference in bacteria count of test articles with or without exposure to S. aureus. This test measures the reduction of bacteria population in a short time, in no growth condition.

| Sample | S. aureus |
|---|---|
| (a) 2% Ag ion exch in Cap/Gly | 0.5 |
| (b) 2% Ag acetate in Cap/Gly | 0 |

(a) Cap/Gly initiated with Glycolic acid (Inventive Sample)
(b) Cap/Gly initiated with Mannitol (Comparative Sample)

Accordingly, the data demonstrate the enhanced efficacy of the antimicrobial anionic polyester complexes of the present invention as compared to antimicrobial salts dispersed in polymer matrices as a mixture.

What is claimed is:

1. An antimicrobial composition comprising an ionic complex of an anionic polyester with antimicrobial metal ions, wherein the anionic polyester has an ion exchange capacity and from about 0.19 meq/g to about 1.0 meq/g of said antimicrobial metal ions are complexed with carboxylic acid groups of said anionic polyester.

2. The antimicrobial composition according to claim 1, wherein the anionic polyester has a weight average molecular weight (Mw) between about 2000 and about 7200 Daltons.

3. The antimicrobial composition according to claim 1, wherein the composition contains from about 20,000 ppm to about 96,000 ppm by weight of the antimicrobial metal ions.

4. The antimicrobial composition according to claim 1, wherein the anionic polyester is prepared from a ring-opening polymerization of aliphatic lactone monomers polymerized in the presence of an organometallic catalyst and an anionic initiator.

5. The antimicrobial composition according to claim 4, wherein the aliphatic lactone monomer is selected from the group consisting of glycolide, trimethylene carbonate, L-lactide, D-lactide, DL-lactide, mesolactide, ε-caprolactone, p-dioxanone, 1,3-dioxan-2-one, δ-valerolactone, β-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, γ-butyrolactone, 1,4-dioxepan-2-one, 1,5-dioxepan-2-one, 6,6-dimethyl-dioxepan-2-one, 6,8-dioxabicycloctane-7-one and combinations thereof.

6. The antimicrobial composition according to claim 4, wherein the anionic initiator is selected from the group consisting of alpha-hydroxy acids, glycolic acid, D-lactic acid, DL-lactic acid, L-lactic acid, β-hydroxyacids, γ-hydroxyacids, δ-hydroxyacids, ε-hydroxyacids, ε-hydroxycaproic acid, polyhydroxyacids, tartaric acid, citric acid and glucoronic acid.

7. The antimicrobial composition according to claim 4, wherein the mole ratio of lactone monomer to initiator is between about 10 and 30.

8. The antimicrobial composition of claim 1 wherein the antimicrobial metal ions are selected from the group consisting of Ag, Au, Pt, Pd, Ir, Sn, Cu, Sb, Bi, Zn, Ni, Mg, and Mn ions.

9. The antimicrobial composition of claim 8, wherein the antimicrobial metal ions are silver ions.

10. The antimicrobial composition of claim 3, wherein the antimicrobial metal ions are silver ions.

11. An antimicrobial composition comprising an ionic complex of an anionic polyester with antimicrobial metal ions, wherein the composition contains from about 20,000 ppm to about 96,000 ppm by weight of the antimicrobial metal ions complexed with said anionic polyester.

12. The antimicrobial composition of claim 4, wherein said lactone monomers are ε-caprolactone and glycolide, and the anionic initiator is glycolic acid.

13. The antimicrobial composition of claim 4, wherein said lactone monomer is ε-caprolactone and the anionic initiator is glycolic acid.

14. The antimicrobial composition of claim 4, wherein said lactone monomers are lactide and glycolide, and the anionic initiator is glycolic acid.

15. An antimicrobial composition comprising an ionic complex of an anionic polyester with antimicrobial metal ions, wherein the anionic polyester has an ion exchange capacity, and from about 0.19 meq/g to about 1.0 meq/g of said antimicrobial metal ions are exchanged for hydrogen atoms of free carboxylic acid groups on said anionic polyester.

* * * * *